United States Patent
Lee et al.

(10) Patent No.: US 10,385,142 B2
(45) Date of Patent: Aug. 20, 2019

(54) METHOD FOR PREPARING SUGAMMADEX SODIUM

(71) Applicant: ScinoPharm Taiwan, Ltd., Shan-Hua, Tainan (TW)

(72) Inventors: ChiaYing Lee, Tainan (TW); ShangHong Chen, Tainan (TW)

(73) Assignee: SCINOPHARM TAIWAN, LTD., Shan-Hua, Tainan (TW)

( * ) Notice: Subject to any disclaimer, the term of this patent is extended or adjusted under 35 U.S.C. 154(b) by 0 days.

(21) Appl. No.: 15/873,505

(22) Filed: Jan. 17, 2018

(65) Prior Publication Data

US 2018/0208683 A1 Jul. 26, 2018

Related U.S. Application Data

(60) Provisional application No. 62/449,139, filed on Jan. 23, 2017.

(51) Int. Cl.
*C08B 37/16* (2006.01)
*C07C 323/52* (2006.01)

(52) U.S. Cl.
CPC ........ *C08B 37/0012* (2013.01); *C07C 323/52* (2013.01)

(58) Field of Classification Search
CPC .................................................. C08B 37/0012

See application file for complete search history.

(56) References Cited

U.S. PATENT DOCUMENTS

| RE44,733 E | 1/2014 | Zhang et al. |
| 9,120,876 B2 | 9/2015 | Davuluri et al. |

(Continued)

FOREIGN PATENT DOCUMENTS

| CN | 105273095 A | 1/2016 |
| WO | 2016194001 A1 | 12/2016 |
| WO | 2017163165 A1 | 9/2017 |

OTHER PUBLICATIONS

Chmurski, K. et al "An improved synthesis of 6-deoxyhalo cyclodextrins . . . " Tet. Lett., vol. 38, No. 42, pp. 7365-7368. (Year: 1997).*

(Continued)

*Primary Examiner* — Leigh C Maier
(74) *Attorney, Agent, or Firm* — Enshan Hong; Kent H. Cheng; VLP Law Group LLP

(57) ABSTRACT

A process for preparing sugammadex sodium comprising:
reacting a γ-cyclodextrin of formula I with a halogenating agent in the presence of N-methyl-2-pyrrolidone to provide a compound of formula II; and
reacting the compound of formula II with 3-mercapto propionic acid in the presence of a sodium base and an organic solvent to provide sugammadex sodium formula III:

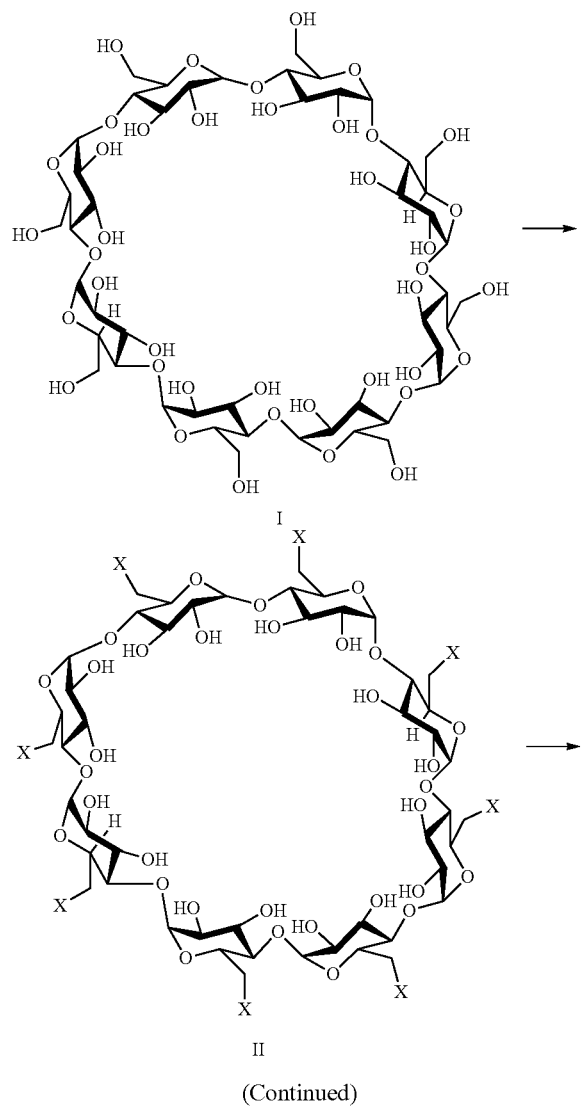

(Continued)

-continued

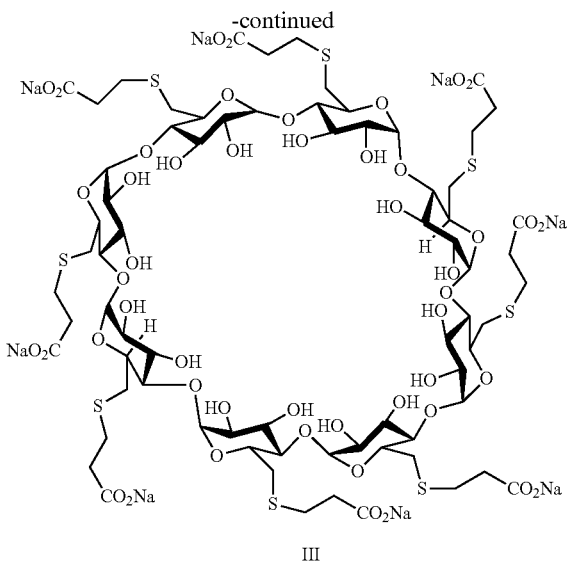

III wherein X in formula II is halo.

18 Claims, No Drawings

(56) References Cited

U.S. PATENT DOCUMENTS

2016/0009827 A1* 1/2016 Ravi .................. C08B 37/0012
536/103
2018/0171033 A1 6/2018 Alaparthi

OTHER PUBLICATIONS

Takeo, K. et al "Animproved synthesis of 6-deoxy-analogues of cyclodextrins . . . " Die Starke, vol. 26, No. 4, pp. 111-118. (Year: 1974).*

Szejtli, J. "Introduction and general overview of cyclodextrin chemistry" Chem. Rev., vol. 98, pp. 1743-1753. (Year: 1998).*

Guillo et al., Bull Soc Chim Fr (1995) 132, 857-866.

Written Opinion of the International Search Authority dated May 11, 2018 for related PCT Application No. PCT/SG2018/050038.

International Search Report dated May 11, 2018 for related PCT Application No. PCT/SG2018/050038.

* cited by examiner

METHOD FOR PREPARING SUGAMMADEX SODIUM

CROSS-REFERENCES TO RELATED APPLICATIONS

This application claims priority from U.S. Provisional Patent Application Ser. No. 62/449,139, which was filed on Jan. 23, 2017. The entire content of this provisional application is incorporated herein by reference.

BACKGROUND OF THE INVENTION

The present invention relates to a process for preparing sugammadex sodium, a modified gamma cyclodextrin chemically designated as 6A,6B,6C,6D,6E,6F,6G,6H-Octakis-S-(2-carboxyethyl)-6A,6B,6C,6D,6E,6F,6G,6H-octathio-γ-cyclodextrin sodium salt (1:8) with a molecular weight of 2178.01 and a formula as shown below:

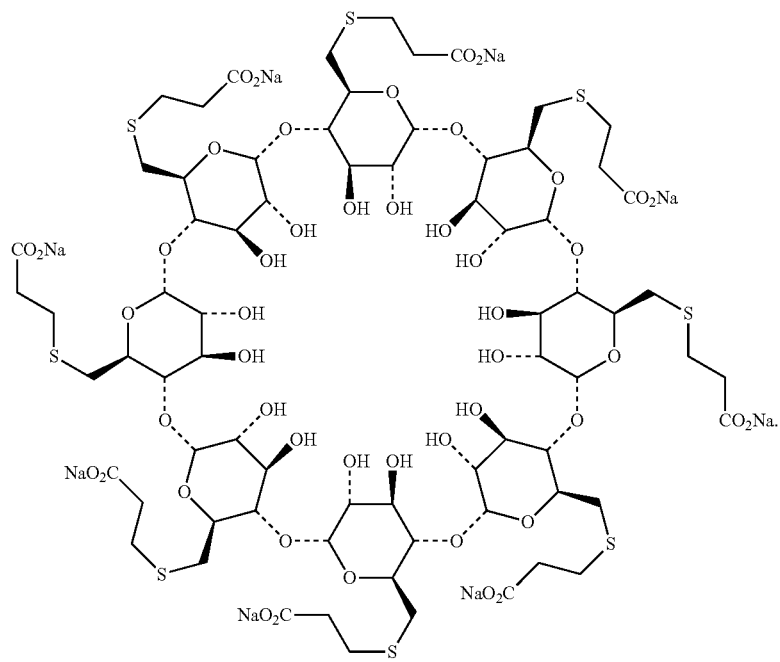

Sugammadex sodium (marked as BRIDION®) is a modified gamma cyclodextrin. It forms a complex with neuromuscular blocking agents rocuronium and vecuronium, and it reduces the amount of neuromuscular blocking agent available to bind to nicotinic cholinergic receptors in the neuromuscular junction. This results in reversal of neuromuscular blockade induced by rocuronium and vecuronium. BRIDION® was approved by the U.S. Food and Drug Administration (FDA) on Dec. 15, 2015.

U.S. Pat. No. RE 44,733 (the '733 patent) describes a preparation method of sugammadax as shown in Scheme 1 below:

Scheme 1: Preparation of Sugammadax Disclosed in USRE44733E
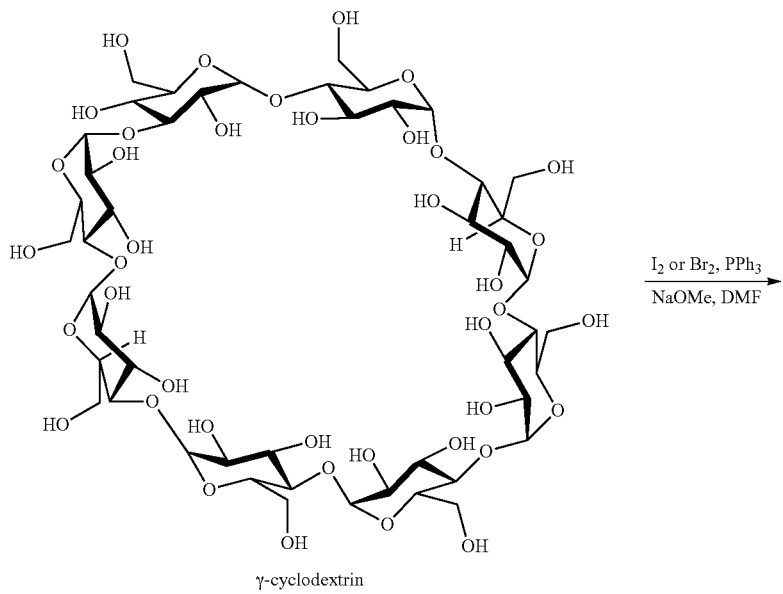
γ-cyclodextrin
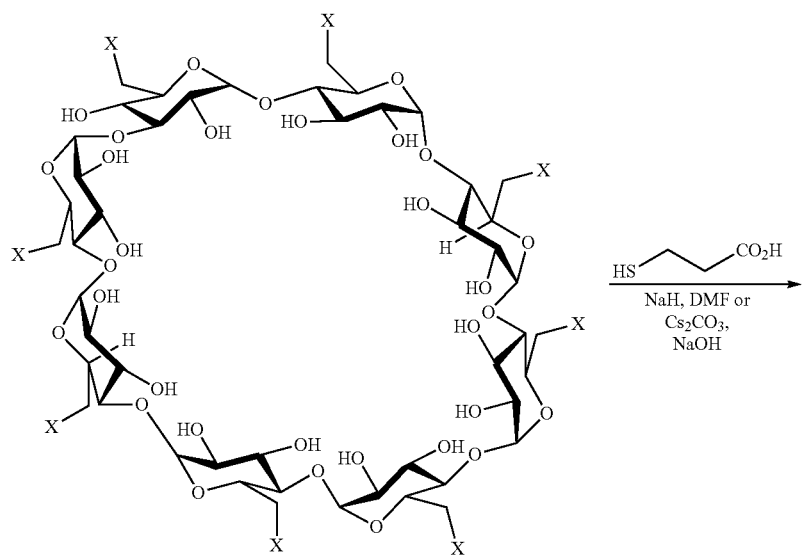

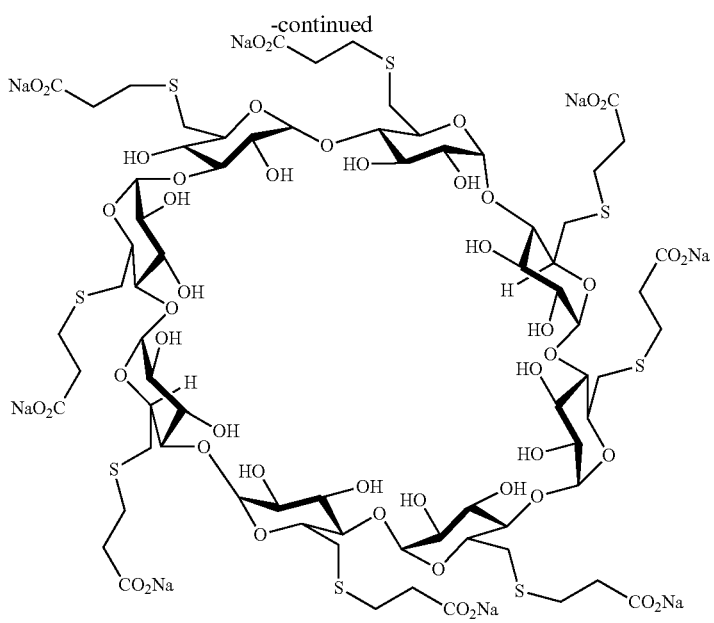

Sugammadex is prepared by dissolving γ-cyclodextrin in $X_2$ ($Cl_2$ or $Br_2$)/$PPh_3$/NaOMe in DMF followed by adding NaH and 3-mercapto propionic acid or NaOH/$Cs_2CO_3$/3-mercapto propionic acid.

A similar approach for sugammadax preparation is reported in U.S. Pat. No. 9,120,876B2 (the '876 patent, Scheme 2 below). Sugammadex is prepared by dissolving γ-cyclodextrin in $PX_3$ or $PX_5$ in DMF followed by adding NaH and 3-mercapto propionic acid. Based on the '733 patent and the '876 patent, $PPh_3$ is used to produce the intermediate, and a significant amount of side product $PPh_3O_2$ is produced. $PPh_3O_2$ is hard to remove, and the intermediate is hard to isolate.

Scheme 2: Preparation of Sugammadax Disclosed in US9120876B2

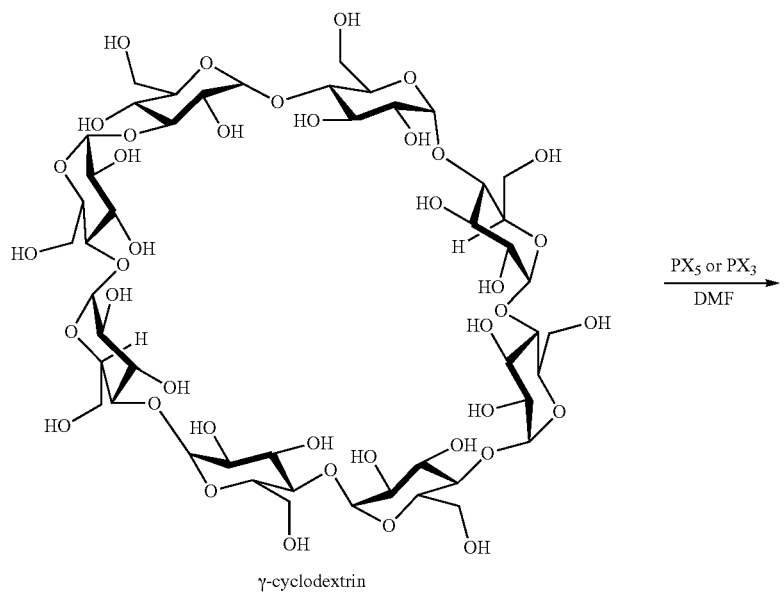

γ-cyclodextrin

-continued
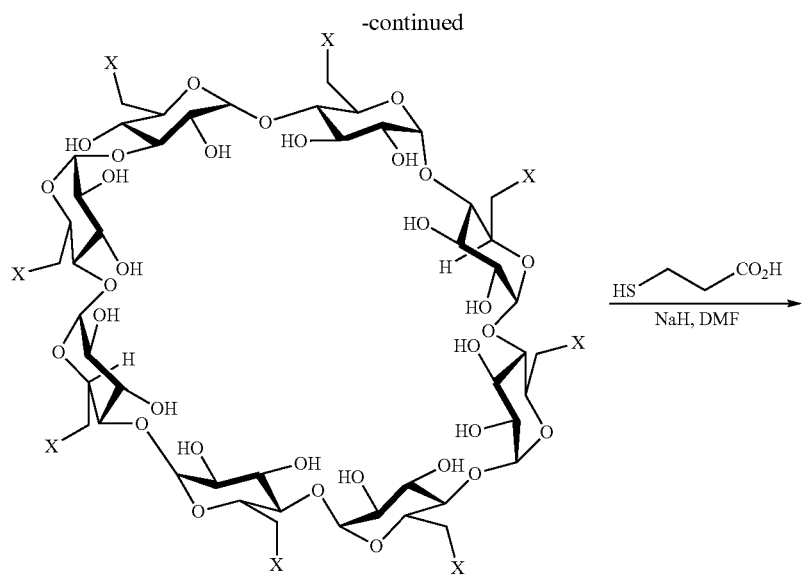
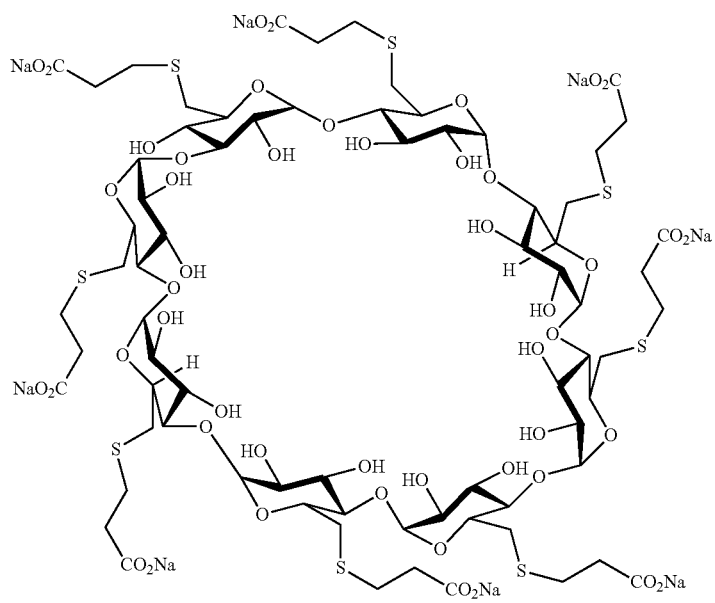
Another synthetic route is reported in Chinese Patent Application CN105273095A (Scheme 3 below). Sugammadex is prepared by dissolving γ-cyclodextrin in oxalyl chloride or $SOCl_2$ in DMF followed by adding NaH and 3-mercapto propionic acid. When oxalyl chloride or $SOCl_2$ is added into the mixture, exothermic heat and HCl are produced.

Scheme 3: Preparation of Sugammadax Disclosed in CN105273059A
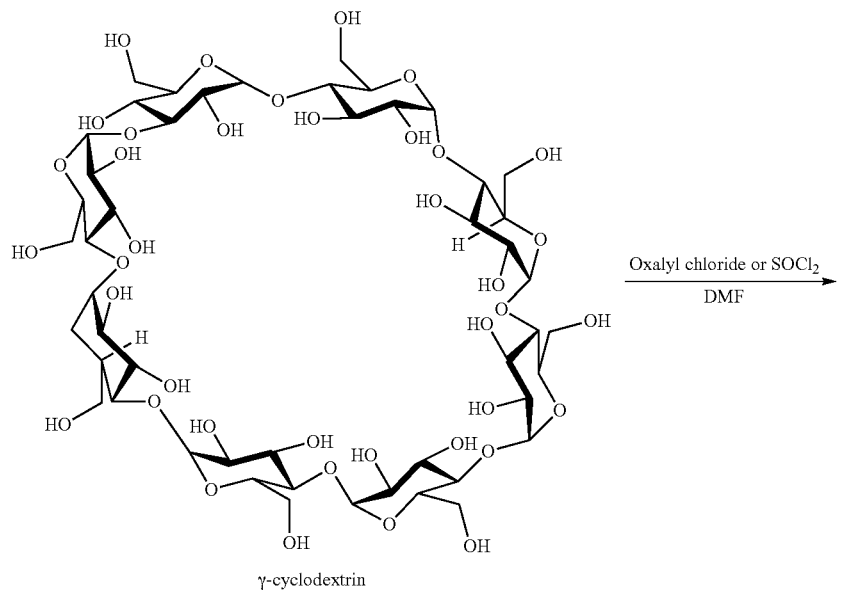
γ-cyclodextrin
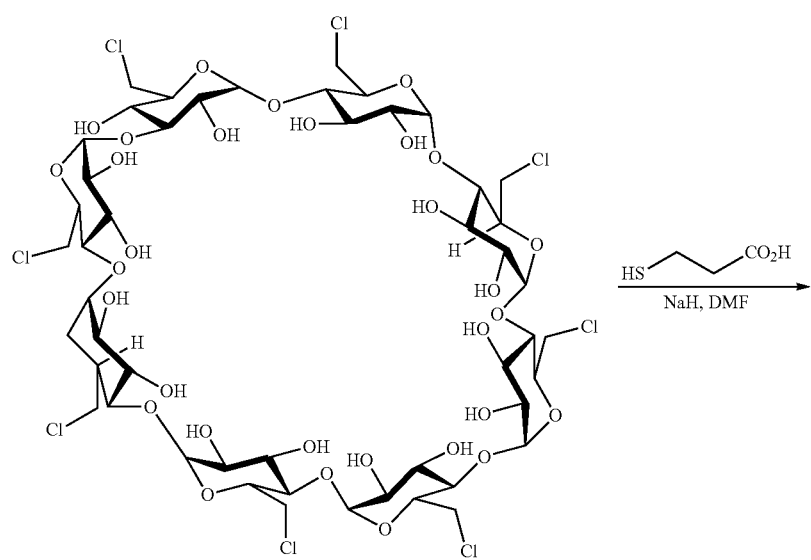

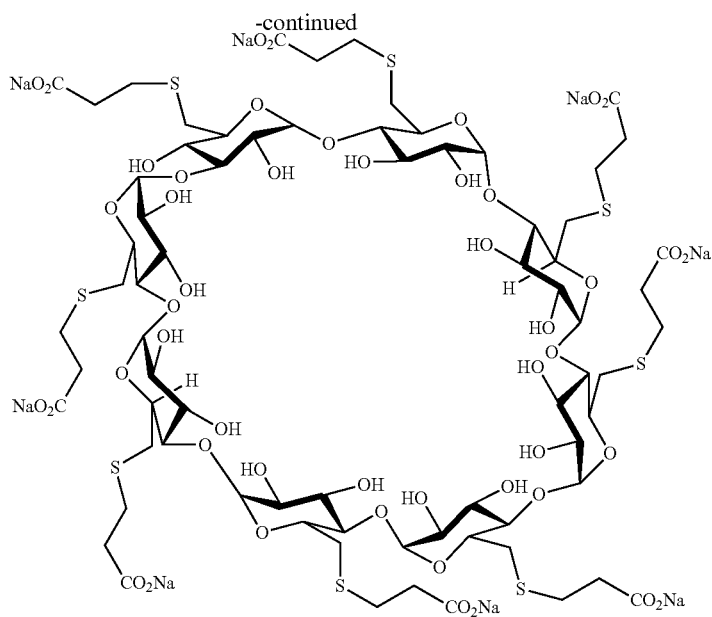

Bull Soc Chim Fr 1995 132 857-866 discloses that halide-γ-cyclodextrin can be prepared by reacting γ-cyclodextrin with MsCl in DMF.

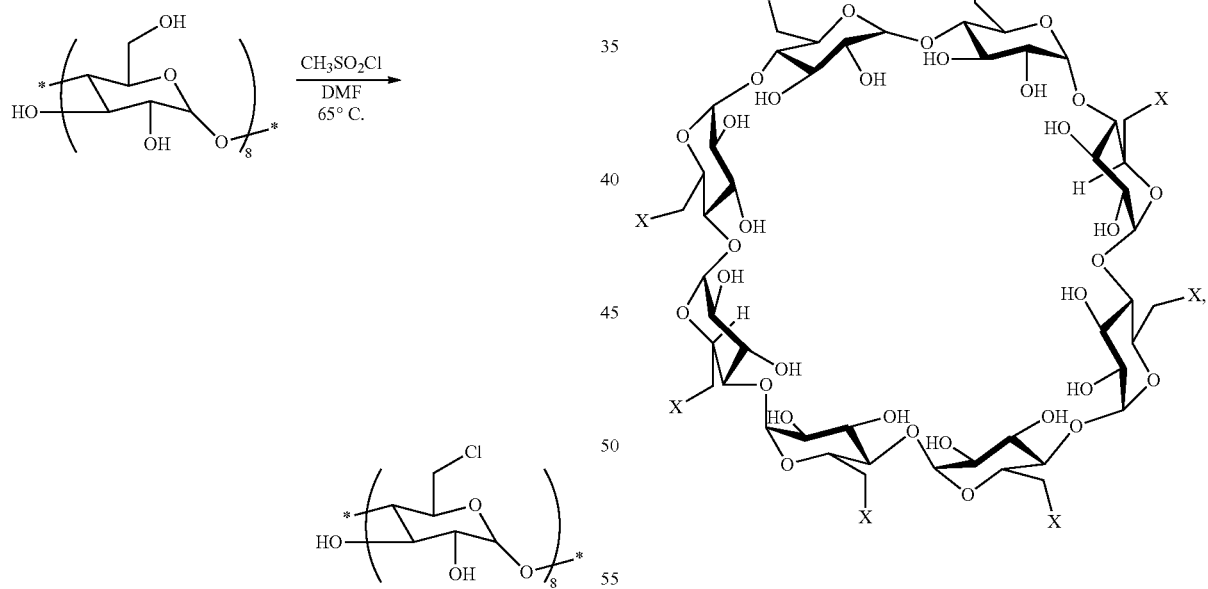

In view of the above, there remains a need for the development of improved processes for the preparation of sugammadax sodium.

SUMMARY OF THE INVENTION

In one aspect, the present application provides a process for preparing a compound of formula II:

wherein X represents a halogen group, preferably chloro.

The process comprises reacting a γ-cyclodextrin of formula I with a halogenating agent in the presence of N-methyl-2-pyrrolidone:

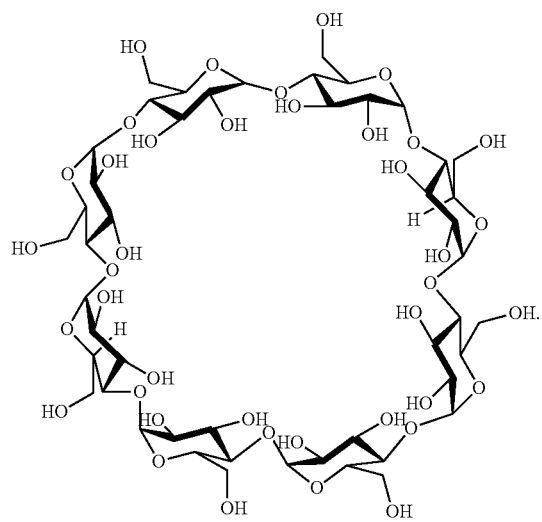

I

In a second aspect, the present application provides a process for preparing a sugammadex salt of formula IIIa

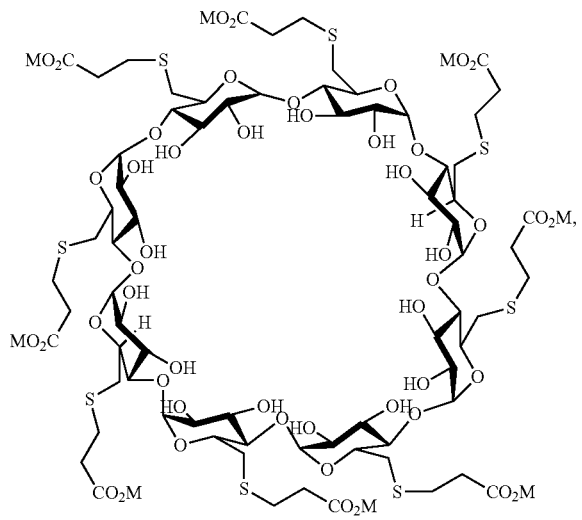

IIIa wherein M represents Na or K, and the process comprises:
a) reacting a γ-cyclodextrin of formula I with a halogenating agent in the presence of N-methyl-2-pyrrolidone to provide a compound of formula II:

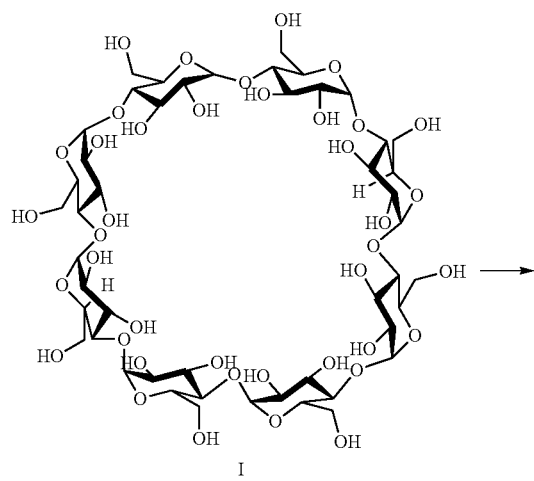

I

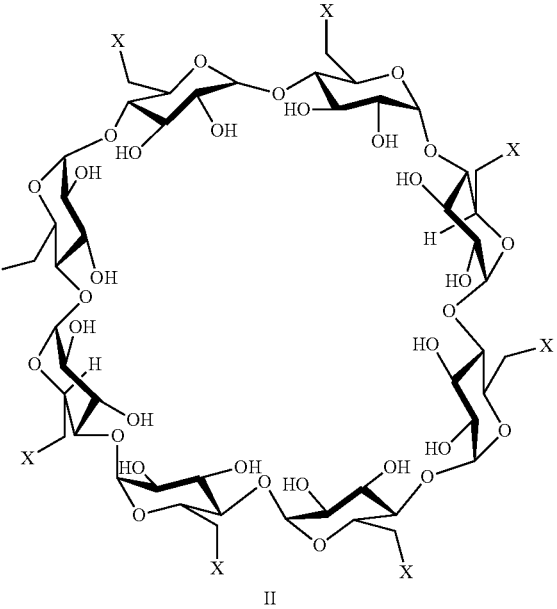

II wherein X is a halogen group, preferably chloro;

b) reacting the compound of formula II with 3-mercapto propionic acid in the presence of a base and an organic solvent to provide a sugammadex salt of formula IIIa:

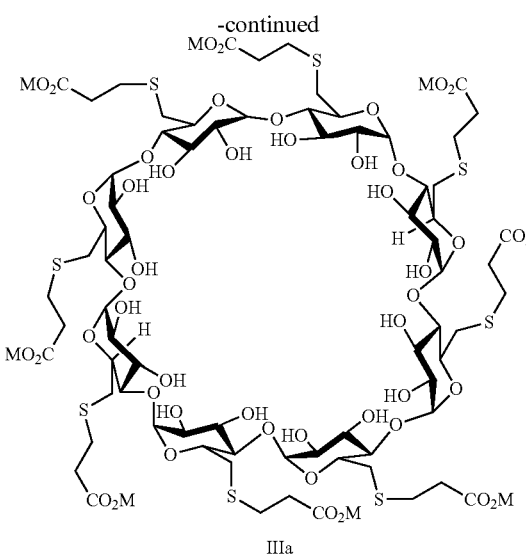

IIIa

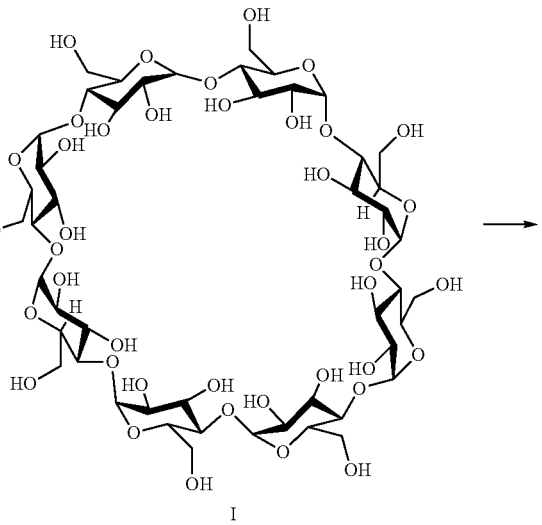

I and c) optionally purifying the sugammadex salt of formula IIIa.

In a third aspect, the present application provides a one-pot process for preparing sugammadex sodium salt of formula III comprising:

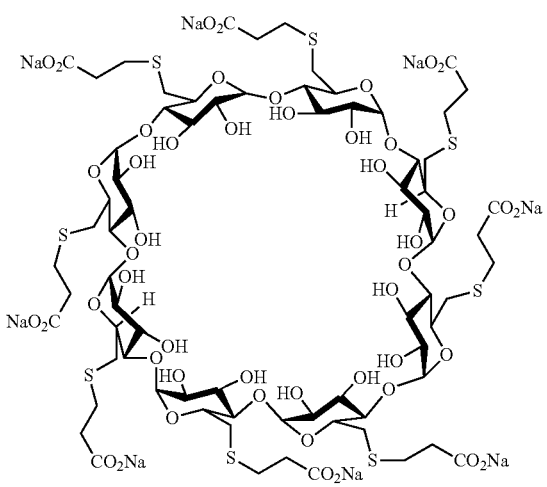

III

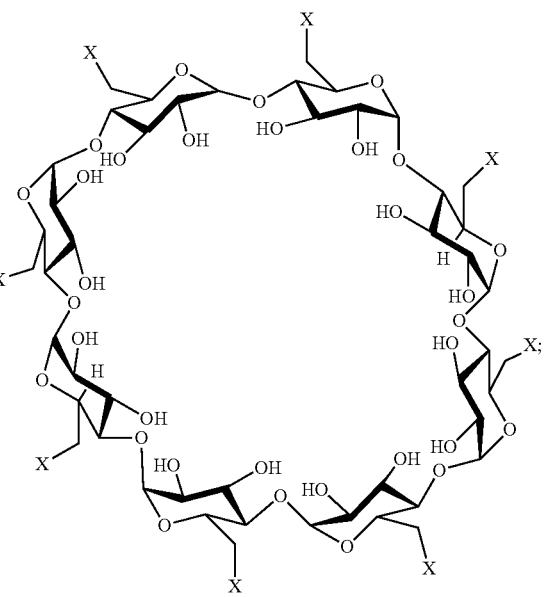

II a) reacting a γ-cyclodextrin of formula I with a halogenating agent in the presence of N-methyl-2-pyrrolidone to provide a compound of formula II:

wherein X is a halogen group, preferably chloro; and b) reacting the compound of formula II with 3-mercapto propionic acid in the presence of an sodium base and an organic solvent to a provide sugammadex sodium of formula III.

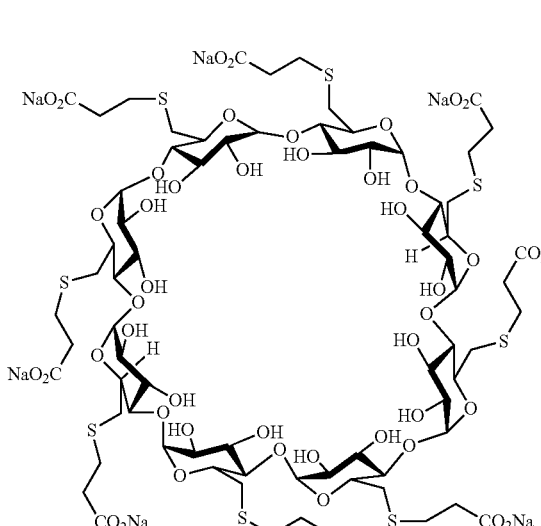

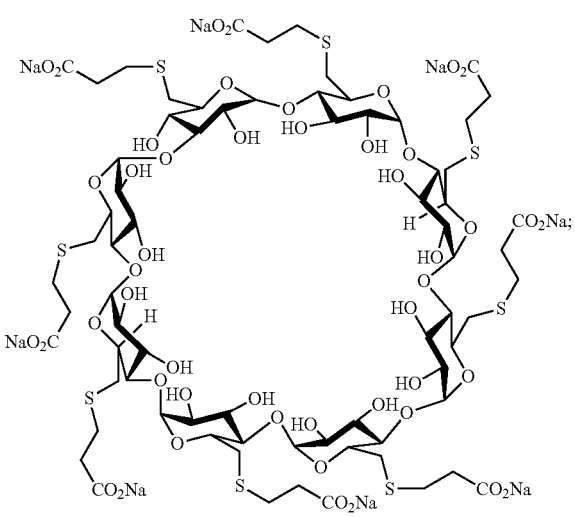

and
c) optionally purifying the sugammadex sodium of formula III.

DETAILED DESCRIPTION OF PREFERRED EMBODIMENTS OF THE INVENTION

The abbreviations used in the present application are defined as following:
DMF: dimethylformamide.
DMSO: dimethyl sulfoxide.
DMAc: dimethylacetamide.
NMP: N-methyl-2-pyrrolidone.

In one aspect, the present application provides a process for preparing a compound of formula II:

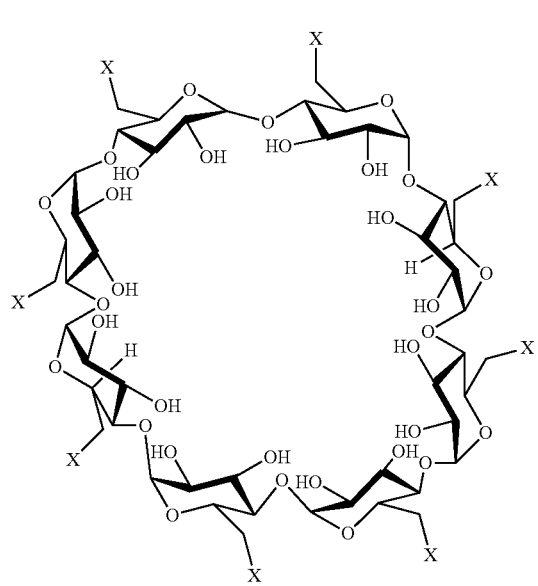

wherein X is a halogen group, preferably chloro.

The process comprises reacting a γ-cyclodextrin of formula I with a halogenating agent in presence of N-methyl-2-pyrrolidone:

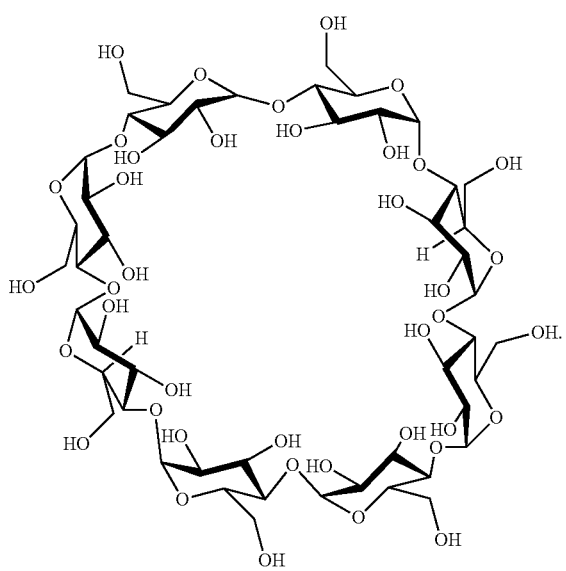

In some embodiments, the temperature of this reaction is maintained from 50-80° C. In some embodiments, the temperature is about 60-70° C. In some embodiments, the halogenating agent is selected from the group consisting of methanesulfonyl chloride, bromine, iodine, N-iodosuccinimide, oxalyl chloride, oxalyl bromide, thionyl chorlide, thionyl bromide, phosphorus trichloride, phosphorus tribromide, phosphorus pentachloride, phosphoruspentabromide, phosphoryl chloride or phosphoryl bromide. In some embodiments, the halogenating agent is preferably methanesulfonyl chloride.

In another aspect, the present application provides a process for preparing sugammadex salt of formula IIIa

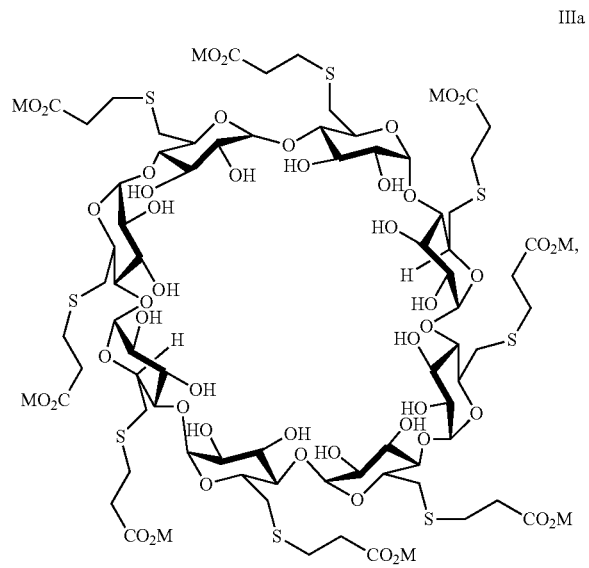

IIIa wherein M represents Na or K and the process comprises:

a) reacting a γ-cyclodextrin of formula I with a halogenating agent in the presence of N-methyl-2-pyrrolidone to provide the compound of formula II:

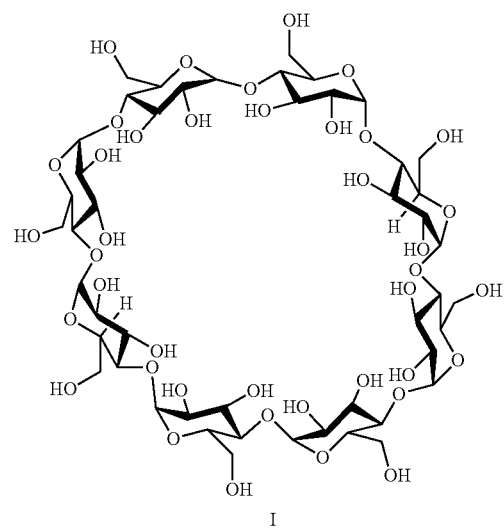

I

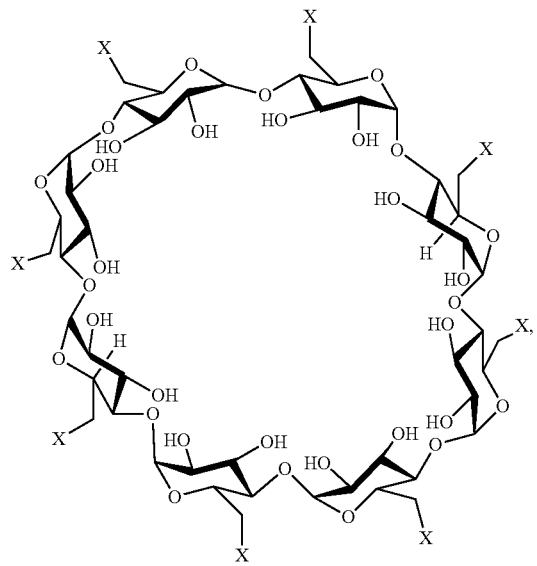

II wherein X is a halogen group, preferably chloro;

b) reacting the compound of formula II with 3-mercapto propionic acid in the presence of a base and an organic solvent to provide the compound of formula IIIa.

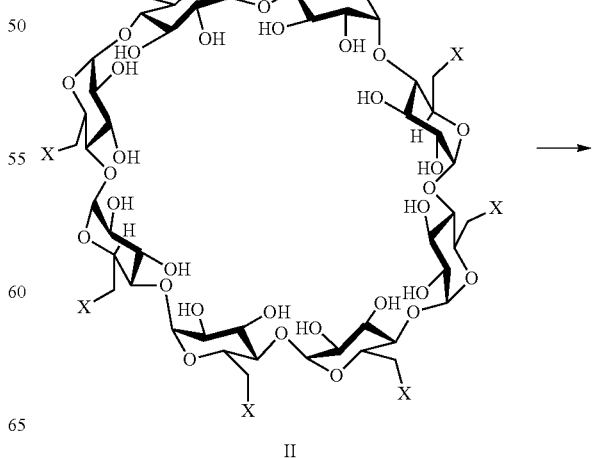

II

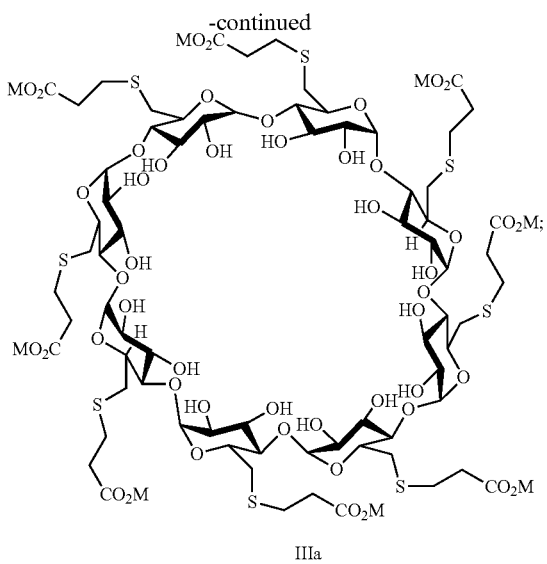

IIIa and
c) optionally, purifying the sugammadex salt of formula IIIa.

In some embodiments, the halogenating agent is selected from the group consisting of methanesulfonyl chloride, bromine, iodine, N-iodosuccinimide, oxalyl chloride, oxalyl bromide, thionyl chorlide, thionyl bromide, phosphorus trichloride, phosphorus tribromide, phosphorus pentachloride, phosphorus pentabromide, phosphoryl chloride or phosphoryl bromide. In some embodiments, the halogenating agent is methanesulfonyl chloride. In some embodiments, the halogenating agent is preferably methanesulfonyl chloride.

In some embodiments, the base of step (b) is selected from alkali metal hydroxide and metal alkoxy. In some embodiments, alkali metal hydroxide is selected from the group consisting of sodium hydroxide, lithium hydroxide, and potassium hydroxide. In some embodiments, the alkali metal hydroxide of step (b) is sodium hydroxide. In some embodiments, the metal alkoxy of step (b) is selected from the group consisting of sodium tert-butoxide (NaOtBu) and sodium methoxide (NaOMe). In some embodiments, the metal alkoxy of step (b) is sodium tert-butoxide (NaOtBu).

In some embodiments, the solvent of step (b) is selected from the group consisting of polar aprotic solvents, $C_{1-5}$ esters, acetonitrile, dimethylformamide, and dimethylsulfoxide. In some embodiments, the solvent of step (b) is preferably dimethylformamide.

In some embodiments, the purification process of sugammadex salt of formula IIIa comprises: c-1) reacting sugammadex salt of formula IIIa with an acid in the presence of a first solvent to provide sugammadex free acid of formula IV: c-2) optionally, purifying the sugammadex free acid of formula IV with chromatograph column or active carbon: and c-3) treating the sugammadex free acid of formula IV with alkali metal hydroxide in the presence of a second solvent.

In some embodiments, the first solvent and/or the second solvent is selected from C1-4 alkyl-alcohols, for example EtOH, MeOH, and IPA. In some embodiments, the first solvent is IPA, and the second solvent is EtOH or MeOH. In some embodiments, the alkali metal hydroxide is sodium hydroxide.

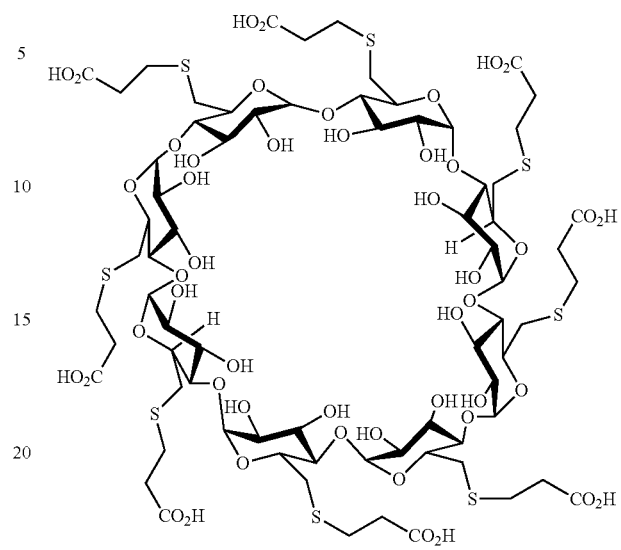

IV

In yet another aspect, the present application provides a one-pot process for preparing sugammadex sodium salt of formula III:

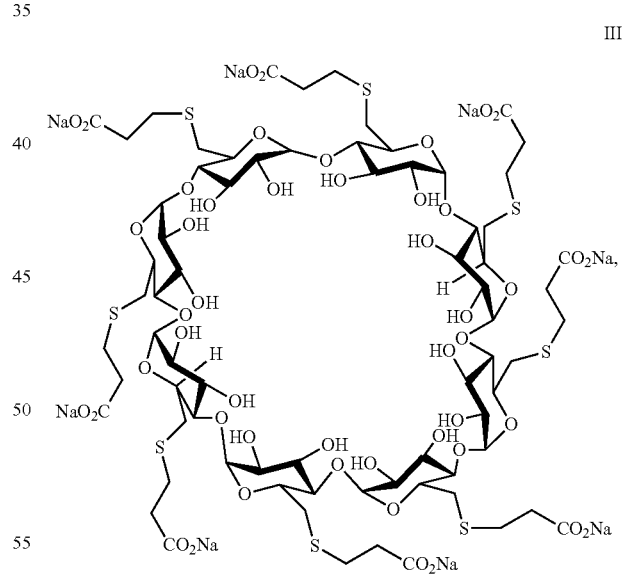

III and the process comprises:
a) reacting a γ-cyclodextrin of formula I with a halogenating agent in the presence of N-methyl-2-pyrrolidone to provide the compound of formula II:

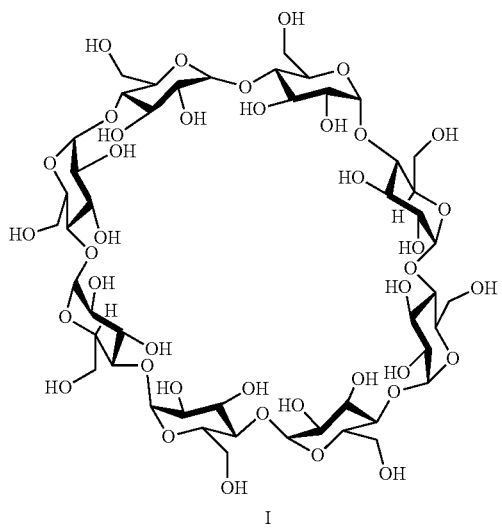

I

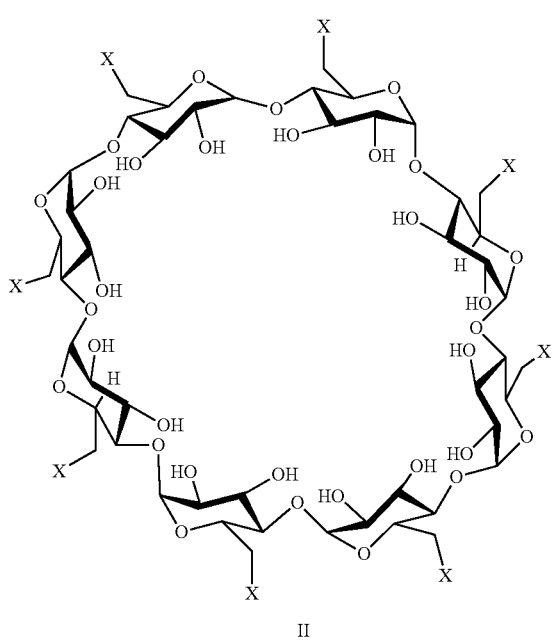

II wherein X is a halogen group, preferably chloro;

b) reacting the compound of formula II with 3-mercapto propionic acid in the presence of a sodium base and an organic solvent to provide the compound of formula III

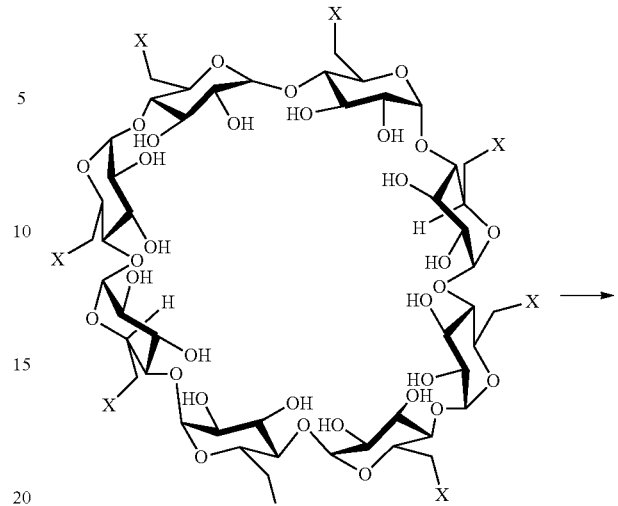

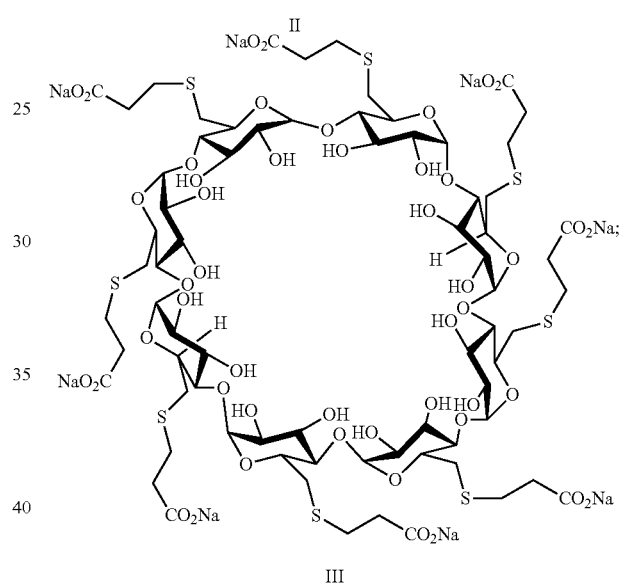

III and c) optionally purifying the sugammadex sodium of formula III.

In some embodiments, the halogenating agent is selected from the group consisting of methanesulfonyl chloride, bromine, iodine, N-iodosuccinimide, oxalyl chloride, oxalyl bromide, thionyl chorlide, thionyl bromide, phosphorus trichloride, phosphorus tribromide, phosphorus pentachloride, phosphorus pentabromide, phosphoryl chloride or phosphoryl bromide. In some embodiments, the halogenating agent is methanesulfonyl chloride. In some embodiments, the halogenating agent is methanesulfonyl chloride.

In some embodiments, the sodium base is selected from sodium hydroxide, sodium tert-butoxide (NaOtBu) or sodium methoxide (NaOMe).

In some embodiments, the solvent of step (b) is selected from the group consisting of polar aprotic solvents, $C_{1-5}$ esters, acetonitrile, dimethylformamide, and dimethylsulfoxide. In some embodiments, the solvent of step (b) is preferably dimethylformamide.

In some embodiments, the purification process of sugammadex sodium of formula III comprises: c-1) reacting sugammadex sodium of formula III with an acid in the presence of a first solvent to provide sugammadex free acid of formula IV: c-2) optionally, purifying the sugammadex free acid of formula IV with chromatograph column or active carbon: and c-3) treating the sugammadex free acid of formula IV with sodium hydroxide in the presence of a second solvent. The acid may be HCl, TFA, $H_3PO_4$, or HOAc.

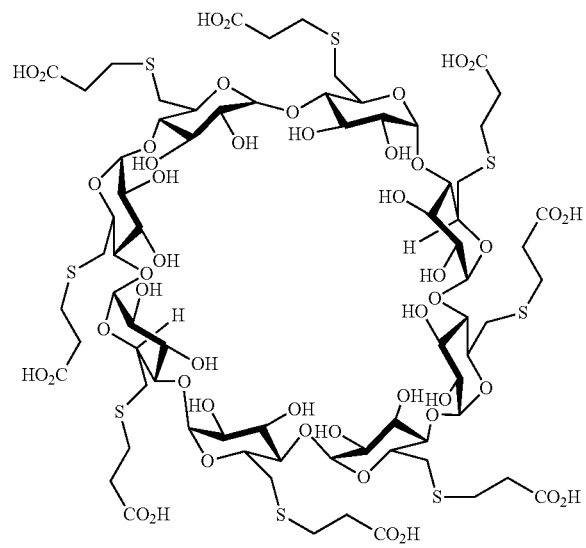

IV

EXAMPLES

The following examples are provided to further illustrate, but not to limit this invention.

Example 1

γ-Cyclodextrin of formula I, methanesulfonyl chloride and N-Methyl-2-pyrrolidone were added into a 500 mL 3-neecked-R-flask at 20-30° C. The mixture was heat to 60-70° C. and stirred for NLT 20 hr. After the reaction was completed, the mixture was cooled to 45-55° C. $H_2O$ and NaOH were added into the mixture at the temperature. The mixture was stirred at for 1 hr and another $H_2O$ was added. The mixture was cooled to 0-10° C. and stirred for NLT 1 hr. The compound of formula II was isolated in 82% yield.

Example 2

3-Mercapto propionic acid, DMSO and NaOH were added into a 50 mL 3-neecked-R-flask at 20-30° C. and the mixture was stirred for 1 hr. The compound of formula II was added at 20-30° C. The mixture was warmed to 70-80° C. and stirred for NLT 12 hr. After the reaction was completed, MeOH was added at 60-80° C. and stirred for 1 hr. The mixture was cooled to 20-30° C. and stirred for 1 hr. The crude sugammadex sodium was isolated and purified as a white solid.

Example 3

γ-Cyclodextrin of formula I, methanesulfonyl chloride and N-Methyl-2-pyrrolidone were added into a 500 mL 3-neecked-R-flask at 20-30° C. The mixture was heat to 60-70° C. and stirred for NLT 20 hr. After the reaction was completed, 3-mercapto propionic acid and NaOH were added into the mixture. The mixture was heated to 70-80° C. and stirred for NLT 12 hr. After the reaction was completed, MeOH was added at 60-80° C. Then the mixture was cooled to 20-30° C. and stirred for 1 hr. The crude sugammadex sodium was isolated and purified as a white solid.

Example 4

3-Mercapto propionic acid, DMSO and NaOtBu were added into a 50 mL 3-neecked-R-flask at 20-30° C. and the mixture was stirred for 1 hr. The compound of formula II was added at 20-30° C. The mixture was warmed to 70-80° C. and stirred for NLT 12 hr. After the reaction was completed, MeOH was added at 60-80° C. and stirred for 1 hr. The mixture was cooled to 20-30° C. and stirred for 1 hr. The crude sugammadex sodium was isolated and purified as a white solid.

Example 5

3-Mercapto propionic acid, DMSO and NaOMe were added into a 50 mL 3-neecked-R-flask at 20-30° C. and the mixture was stirred for 1 hr. The compound of formula II was added at 20-30° C. The mixture was warmed to 70-80° C. and stirred for NLT 12 hr. After the reaction was completed, MeOH was added at 60-80° C. and stirred for 1 hr. The mixture was cooled to 20-30° C. and stirred for 1 hr. The crude sugammadex sodium was isolated and purified as a white solid.

Example 6

The compound of formula III was purified with IPA/$H_2O$/HCl at 40-50° C., and the pH was maintained at 3-4, the resulting the formula IV (sugammadex free acid) was isolated in 60-70% yield.

Example 7

The compound of formula IV was purified with RP-18 silica gel (or active carbon). The resulting the formula IV (sugammadex free acid) was isolated in 50-70% yield.

Example 8

The compound of formula IV was purified with EtOH/$H_2O$/NaOH at 40-50° C., and the pH was maintained at 7-9. The resulting the formula III (sugammadex sodium) was isolated in 60-70% yield.

Comparative Examples

Several other solvents were used to replace N-Methyl-2-pyrrolidone tested in Example 1 above. The specific conditions are listed Table 1 below. Except for the conditions that are explicitly listed in Table 1 below, other conditions and process steps for Comparative Examples 1-3 are the same as those described in Example 1. Specifically, comparative Example 1 was conducted based on page 862, left column, second full paragraph of Bull Soc Chim Fr 1995 132 857-866.

TABLE 1

| No. | Comparative Example 1 | Comparative Example 2 | Comparative Example 3 | Example 1 Shown above |
|---|---|---|---|---|
| Solvent | DMF | DMSO | DMAc | NMP |
| Formula II (gama-cyclodextrin) (g) | 5 | 1.0 | 1.0 | 1.0 |
| yield (g/%) | 5.3/95 | No detective amount-- | No detective amount-- | 0.91/82 |
| Purity (%) | 28.79 | N/A-- | N/A | 93.72 |
| Conversion rate (%) | 27.35 | 0-- | 0-- | 76.85 |

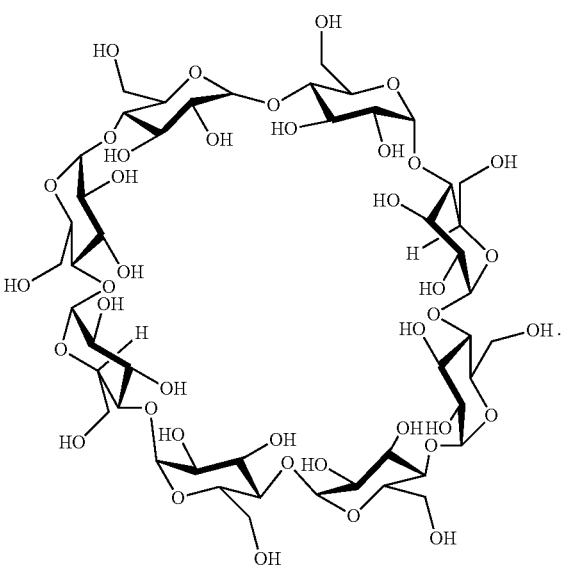

What is claimed is:

1. A process for preparing a compound of formula II:

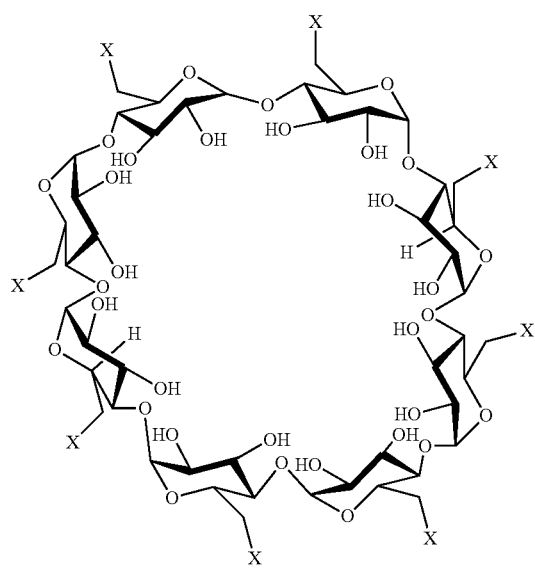

wherein X is a halogen group,
said process comprising reacting a γ-cyclodextrin of formula I with the halogenating agent, methanesulfonyl chloride, in presence of N-Methyl-2-pyrrolidone:

2. The process according to claim 1 comprising conducting the reacting step at about 50-80° C.

3. The process according to claim 1 comprising conducting the reacting step at about 60-70° C.

4. A process for preparing a sugammadex salt of formula IIIa

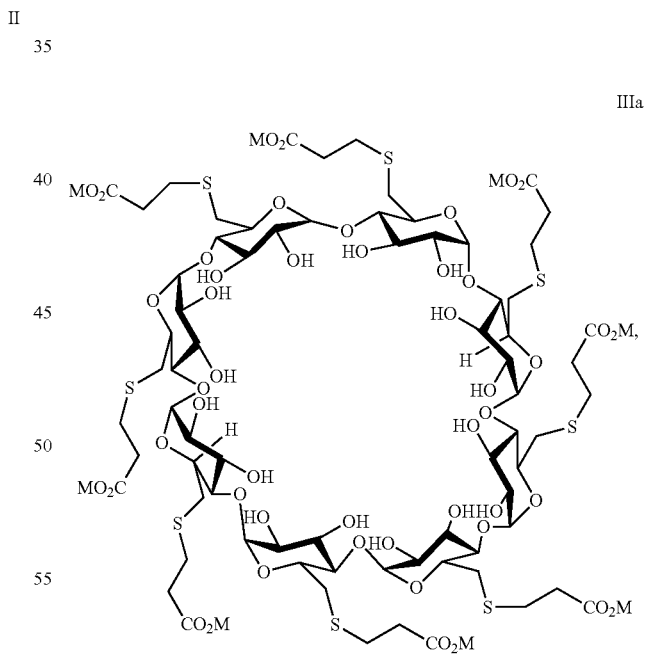

wherein M represents Na or K, and the process comprises:
a) reacting a γ-cyclodextrin of formula I with the halogenating agent, methanesulfonyl chloride, in the presence of N-methyl-2-pyrrolidone to provide a compound of formula II:

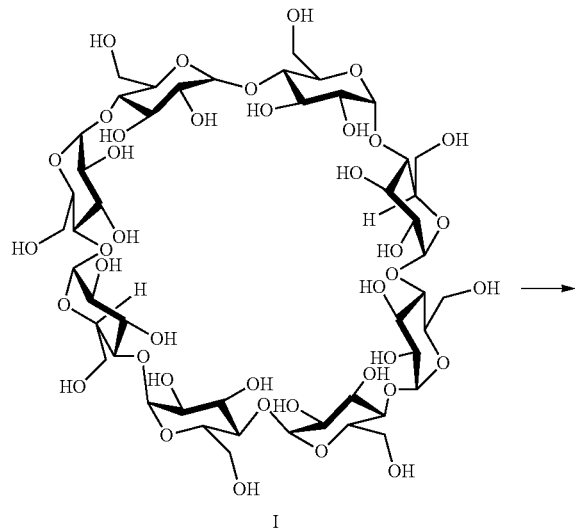

I

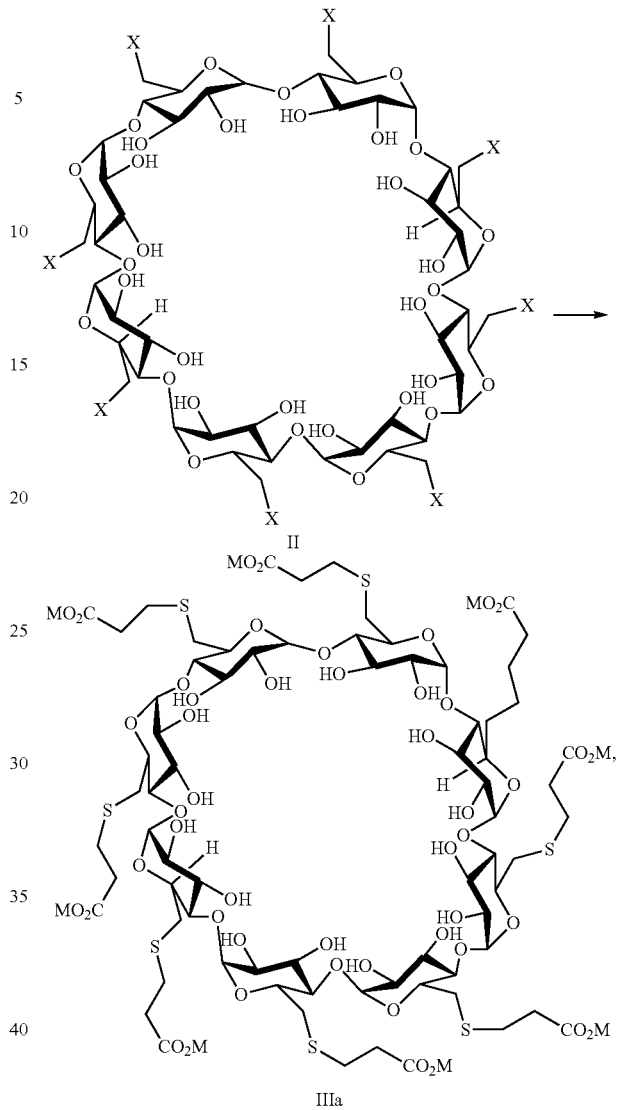

II

IIIa

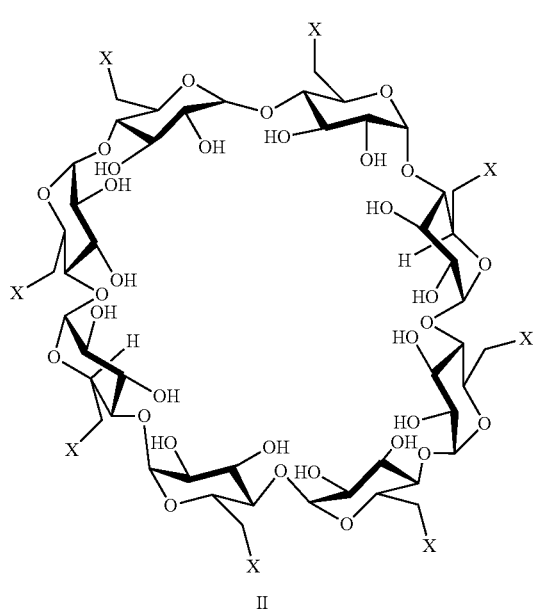

II wherein X is a halogen group, b) reacting the compound of formula II with 3-mercapto propionic acid in presence of a base and an organic solvent to provide a sugammadex salt of formula IIIa:

and c) optionally purifying the sugammadex salt of formula IIIa.

5. The process according to claim 4, wherein the base of step (b) is selected from the group consisting of alkali metal hydroxides and metal alkoxides.

6. The process according to claim 5, wherein the alkali metal hydroxides comprise sodium hydroxide, lithium hydroxide, and potassium hydroxide.

7. The process according to claim 4, wherein the base of step (b) is sodium hydroxide.

8. The process according to claim 5, wherein the metal alkoxides comprise sodium tert-butoxide (NaOtBu) and sodium methoxide (NaOMe).

9. The process according to claim 5, wherein the base of step (b) is sodium tert-butoxide (NaOtBu).

10. The process according to claim 4, wherein the solvent of step (b) is selected from the group consisting of polar aprotic solvents, C1-5 esters, acetonitrile, dimethylformamide, and dimethylsulfoxide.

11. The process according to claim 4, wherein the organic solvent is dimethylformamide.

12. The process according to claim 4 wherein the step c) is conducted and comprises:
c-1) reacting the sugammadex salt of formula IIIa obtained in step b) with an acid in the presence of a first solvent to provide sugammadex free acid of formula IV

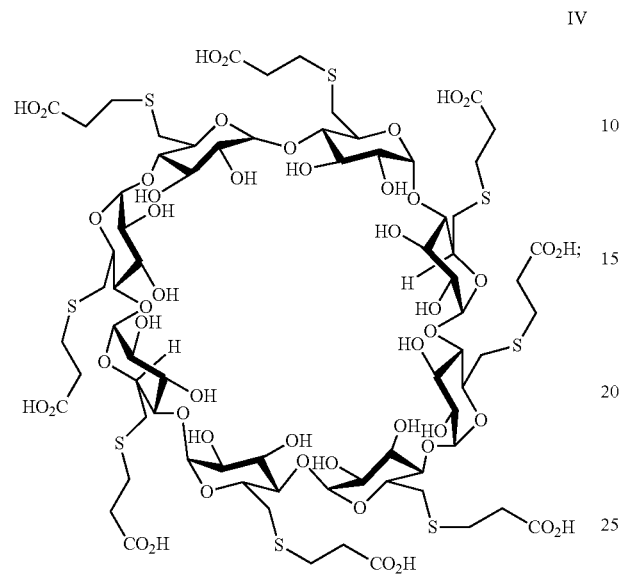

IV c-2) optionally purifying the sugammadex free acid of formula IV with chromatograph column or active carbon; and
c-3) treating the sugammadex free acid of formula IV with an alkali metal hydroxide in presence of a second solvent.

13. The process according to claim 12, wherein the first and second solvent are both independently selected from $C_{1-4}$ alkyl alcohols.

14. The process according to claim 12, wherein the first solvent is isopropyl alcohol, and the second solvent is MeOH.

15. The process according to claim 12, wherein the alkali metal hydroxide is sodium hydroxide.

16. A one-pot process for preparing a sugammadex sodium salt of formula III comprising:

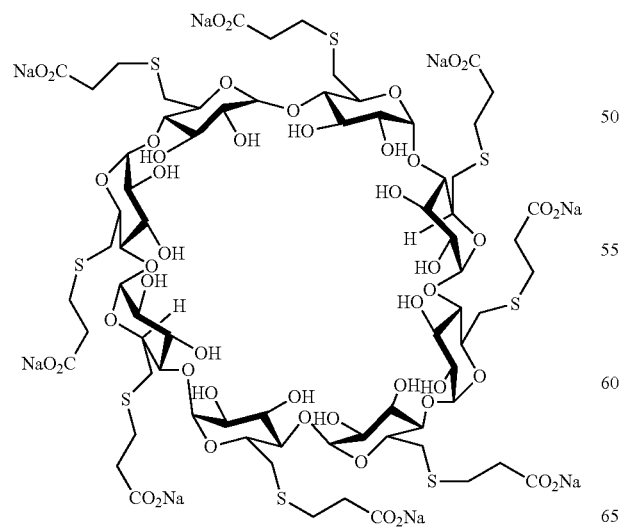

III a) reacting a γ-cyclodextrin of formula I with the halogenating agent, methanesulfonyl chloride, the in presence of N-methyl-2-pyrrolidone to provide a compound of formula II:

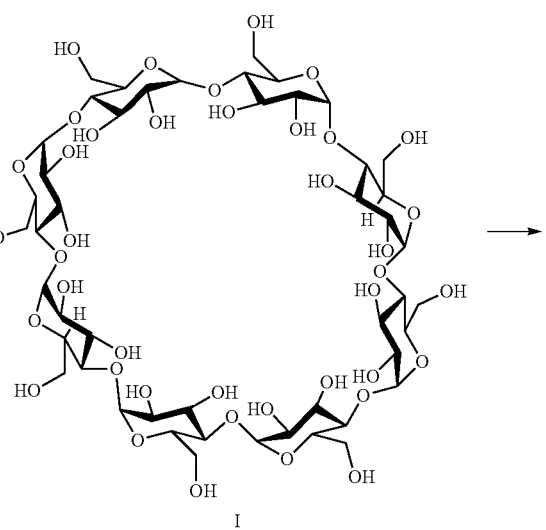

I

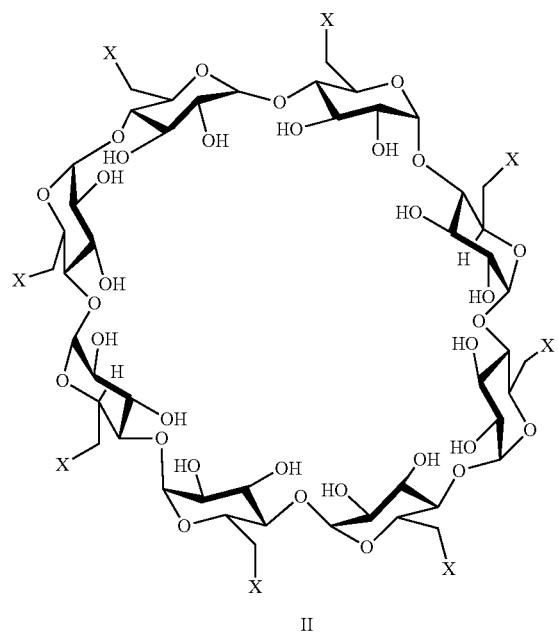

II wherein X is a halogen group;
b) reacting the compound of formula II with 3-mercapto propionic acid in presence of a sodium base and an organic solvent to provide the compound of formula III

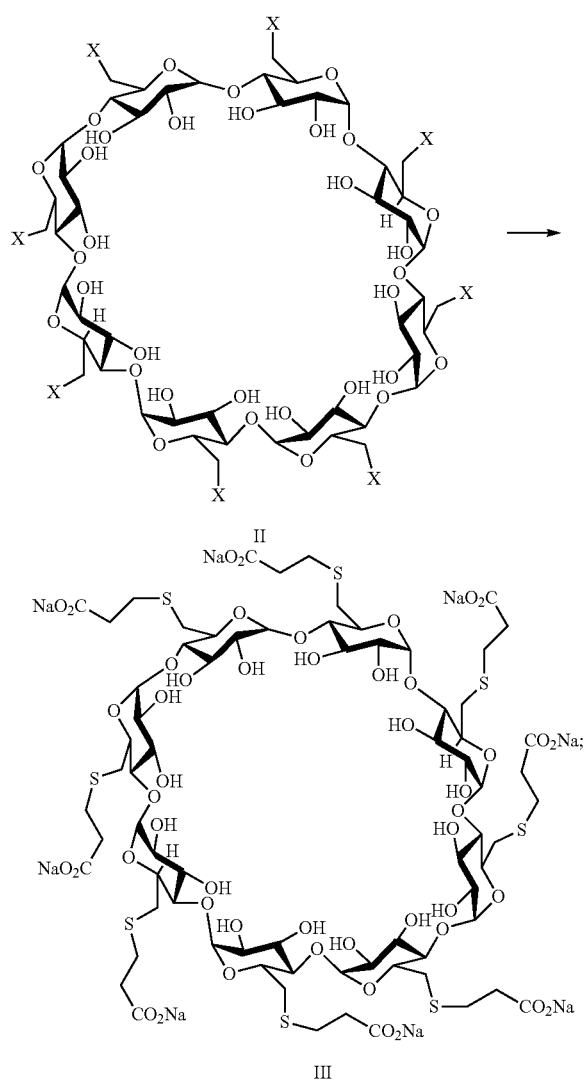

II

III

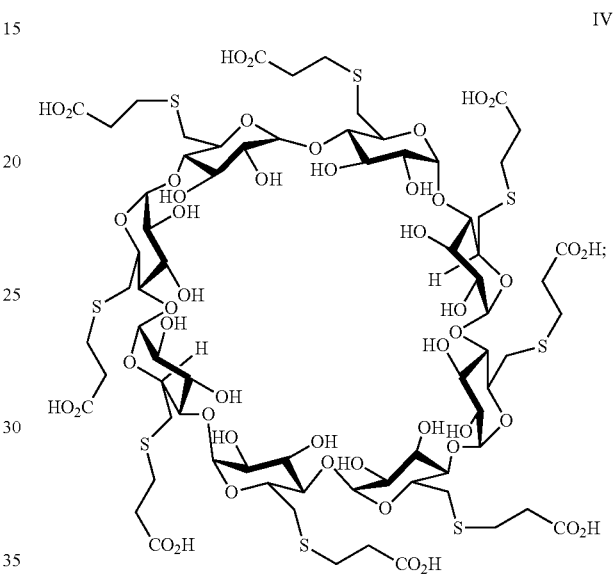

IV and
c) optionally purifying the sugammadex sodium of formula III.

17. The process according to claim 16 wherein the sodium base is selected from the group consisting of sodium hydroxide, sodium tert-butoxide (NaOtBu), and sodium methoxide (NaOMe).

18. The process according to claim 16, wherein the step c) is conducted and comprises:
c-1) reacting the sugammadex sodium of formula III with an acid in the presence of a first solvent to provide a sugammadex free acid of formula IV c-2) optionally purifying the sugammadex free acid of formula IV with chromatograph column or active carbon; and
c-3) treating the sugammadex free acid of formula IV with sodium hydroxide in the presence of a second solvent.

* * * * *